(12) United States Patent
Robinson et al.

(10) Patent No.: US 9,421,309 B2
(45) Date of Patent: Aug. 23, 2016

(54) REDUCED-PRESSURE TREATMENT SYSTEMS AND METHODS EMPLOYING HYDROGEL RESERVOIR MEMBERS

(75) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1380 days.

(21) Appl. No.: 12/786,188

(22) Filed: May 24, 2010

(65) Prior Publication Data

US 2010/0305526 A1  Dec. 2, 2010

Related U.S. Application Data

(60) Provisional application No. 61/183,285, filed on Jun. 2, 2009.

(51) Int. Cl.
*A61M 1/00* (2006.01)
*A61L 15/00* (2006.01)

(52) U.S. Cl.
CPC ............ *A61M 1/0001* (2013.01); *A61M 1/0088* (2013.01); *A61M 2205/8206* (2013.01)

(58) Field of Classification Search
USPC .......................................................... 604/319
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed Sep. 6, 2010 for PCT Application No. PCT/US2010/036080.

(Continued)

*Primary Examiner* — Adam Marcetich
*Assistant Examiner* — Guy K Townsend (57) ABSTRACT

A reduced-pressure treatment system for treating a tissue site of a patient, the system includes a manifold pad for disposing proximate the tissue site. The manifold pad includes a hydrogel reservoir member and a manifold member. The hydrogel reservoir member is adapted to receive and store fluid from the tissue site at a first pressure and adapted to release at least a portion of the fluid at a second pressure. The first pressure is greater than the second pressure on an absolute pressure scale. The system also includes a sealing drape for placing over the tissue and manifold pad. The sealing drape forms a fluid seal over the tissue and manifold pad. A reduced-pressure subsystem delivers reduced pressure to the sealing drape. Other systems, apparatuses, and methods are disclosed.

17 Claims, 5 Drawing Sheets

(56) References Cited

U.S. PATENT DOCUMENTS

| | | |
|---|---|---|
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,204,110 A | 4/1993 | Cartmell et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,423,736 A | 6/1995 | Cartmell et al. |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,329,565 B1* | 12/2001 | Dutkiewicz ......... A61F 13/5323 442/334 |
| 6,345,623 B1 | 2/2002 | Heaton et al. |
| 6,488,643 B1 | 12/2002 | Tumey et al. |
| 6,493,568 B1 | 12/2002 | Bell et al. |
| 6,515,075 B1 | 2/2003 | Balogh et al. |
| 6,553,998 B2 | 4/2003 | Heaton et al. |
| 6,814,079 B2 | 11/2004 | Heaton et al. |
| 6,979,324 B2* | 12/2005 | Bybordi ............... A61M 27/00 604/313 |
| 7,070,584 B2 | 7/2006 | Johnson et al. |
| 7,105,629 B2 | 9/2006 | Matsuda |
| 7,520,872 B2* | 4/2009 | Biggie ................ A61M 1/0088 601/6 |
| 7,700,819 B2* | 4/2010 | Ambrosio ............. A61L 27/52 602/41 |
| 7,731,702 B2* | 6/2010 | Bybordi ............... A61M 27/00 601/10 |
| 8,029,498 B2* | 10/2011 | Johnson ............... A61B 17/88 604/27 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0054338 A1* | 3/2004 | Bybordi ............... A61M 27/00 604/313 |
| 2005/0137539 A1* | 6/2005 | Biggie ................ A61M 1/0096 604/313 |
| 2005/0261643 A1* | 11/2005 | Bybordi ............... A61M 27/00 604/313 |
| 2007/0185426 A1 | 8/2007 | Ambrosio |
| 2007/0218101 A1* | 9/2007 | Johnson ................ A61B 17/88 424/423 |
| 2007/0219471 A1* | 9/2007 | Johnson ................ A61B 17/88 601/6 |
| 2007/0219585 A1* | 9/2007 | Cornet ................ A61B 17/88 606/221 |
| 2007/0225663 A1* | 9/2007 | Watt ..................... A61F 13/02 604/313 |
| 2007/0237812 A1 | 10/2007 | Patel |
| 2008/0033324 A1* | 2/2008 | Cornet ................. A61B 17/88 601/6 |
| 2008/0132602 A1 | 6/2008 | Rizk |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |

(56) References Cited

FOREIGN PATENT DOCUMENTS

| WO | WO 90/10424 | | 9/1990 |
|---|---|---|---|
| WO | WO 93/09727 | | 5/1993 |
| WO | WO 94/20041 | | 9/1994 |
| WO | WO 96/05873 | | 2/1996 |
| WO | WO 97/18007 | | 5/1997 |
| WO | WO 99/13793 | | 3/1999 |
| WO | WO 2005/123170 | * | 12/2005 |
| WO | WO 2005/123170 A1 | | 12/2005 |
| WO | WO 2008/086397 A2 | | 7/2008 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants "The Use of Hypermia in the Postoperative Treatment of Lesions of the Extremities and Thorax, "*Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

* cited by examiner

REDUCED-PRESSURE TREATMENT SYSTEMS AND METHODS EMPLOYING HYDROGEL RESERVOIR MEMBERS

RELATED APPLICATION

The present invention claims the benefit, under 35 USC §119(e), of the filing of U.S. Provisional Patent Application Ser. No. 61/183,285, entitled "Reduced-Pressure Treatment Systems and Methods Employing Hydrogel Reservoir Members," filed Jun. 2, 2009, which is incorporated herein by reference for all purposes.

BACKGROUND

The present disclosure relates generally to medical treatment systems and, more particularly, but not by way of limitation, to reduced-pressure treatment systems and methods employing hydrogel reservoir members.

Tissue that is exposed to moisture for extended periods of time runs the risk of maceration and other issues. In order to promote healing, decrease the risk of infection, as well as decrease the risk of maceration, it is often advantageous to remove fluids from the tissue site. Negative pressure wound therapy may be used to remove fluids from the tissue site. With conventional negative pressure wound therapy, however, the tissue may be exposed to moisture for extended periods of time when negative pressure is not being delivered to the tissue.

SUMMARY

Improvements to existing wound care systems, apparatuses, and methods are addressed by the illustrative systems, apparatuses, and methods of the illustrative, non-limiting embodiments herein. According one illustrative, non-limiting embodiment, a reduced-pressure treatment system for treating a tissue site on a patient includes a manifold pad, a sealing drape for placing over the tissue site to form a fluid seal, and a reduced-pressure subsystem for delivering reduced pressure to the manifold pad. The manifold pad includes a manifold member for disposing proximate to the tissue site and a hydrogel reservoir member associated with the manifold member. The hydrogel reservoir member is adapted to receive and store a fluid from the tissue site at a first pressure and adapted to release at least a portion of the fluid at a second pressure, wherein the first pressure is greater than the second pressure on an absolute pressure scale.

According to another illustrative, non-limiting embodiment, a manifold pad for treating a tissue site on a patient includes a manifold member, which is adapted to distribute reduced pressure, and a hydrogel reservoir member associated with the manifold member. The hydrogel reservoir member is adapted to receive and store fluid from the tissue site at a first pressure and adapted to release at least a portion of the fluid at a second pressure. The first pressure is greater than the second pressure on an absolute pressure scale.

According to another illustrative, non-limiting embodiment, a method for treating a tissue site on a patient includes the steps of: placing a manifold pad, which has a hydrogel reservoir member, proximate to the tissue site; disposing a sealing drape over the manifold member and a patient's epidermis; forming a fluid seal between the sealing drape and the patient's epidermis; and delivering reduced pressure to the manifold pad. The hydrogel reservoir member is operable to receive fluid from the tissue site at a first pressure and operable to release at least a portion of the fluid at a second pressure. The first pressure is greater than the second pressure on an absolute pressure scale.

According to still another illustrative, non-limiting embodiment, a method of manufacturing a manifold pad for treating a tissue site on a patient includes the steps of: forming a manifold member; and associating a hydrogel reservoir member with the manifold member. The hydrogel reservoir member is adapted to receive and hold fluid from the tissue site at a first pressure and adapted to release at least a portion of the fluid at a second pressure.

Other features and advantages of the illustrative, non-limiting embodiments will become apparent with reference to the drawings and detailed description that follow.

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the inventions, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1A:
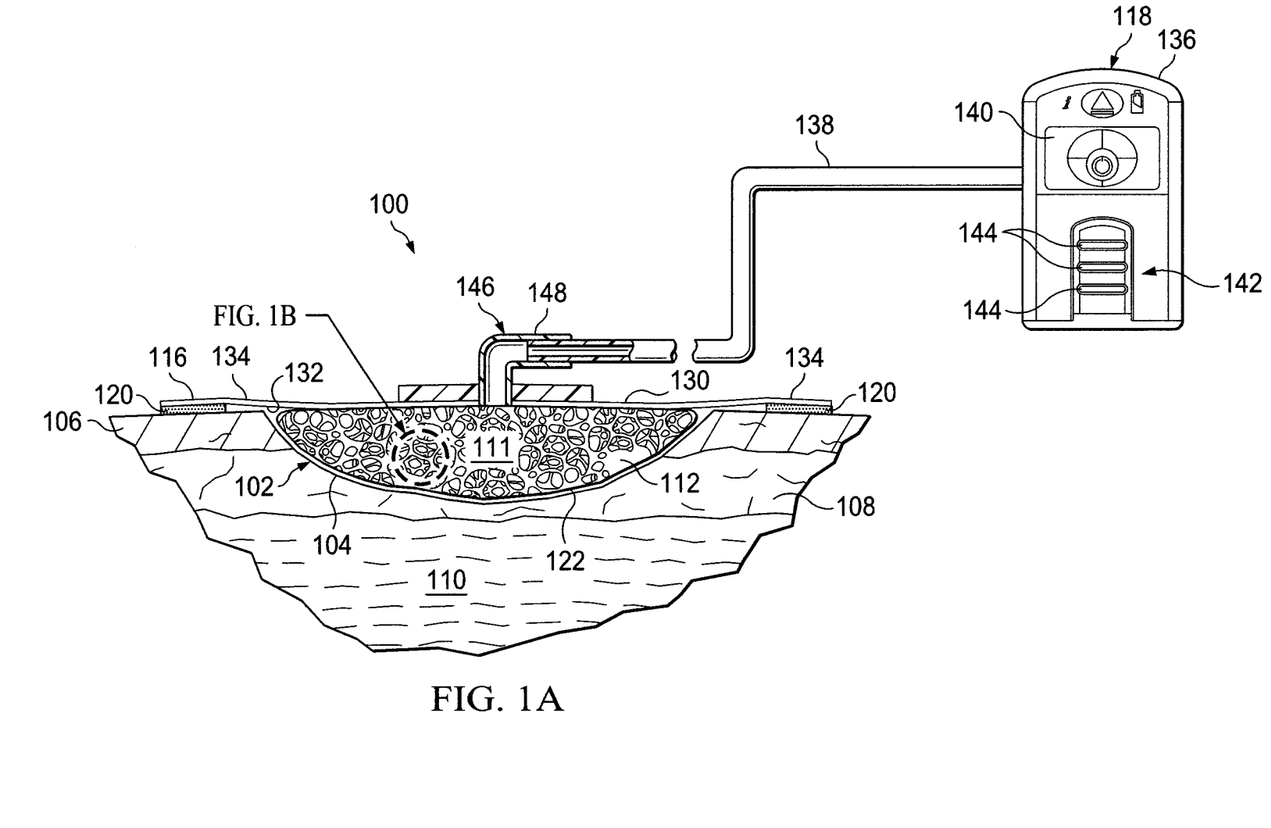
FIG. 1A is a schematic diagram with a portion shown in cross section of an illustrative, non-limiting embodiment of a reduced-pressure treatment system employing a hydrogel reservoir member.
Figure 1B:
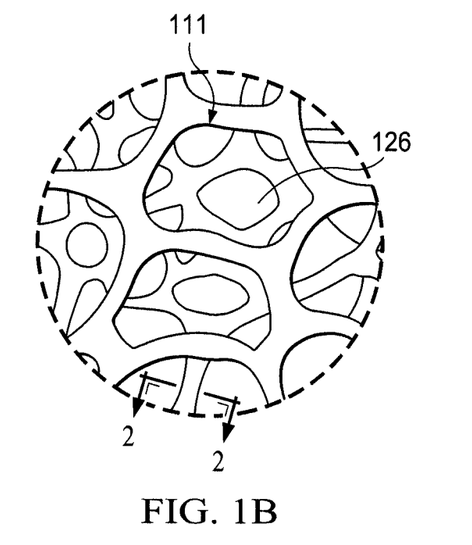
FIG. 1B is an enlarged view of area 1B in FIG. 1A.
Figure 2:
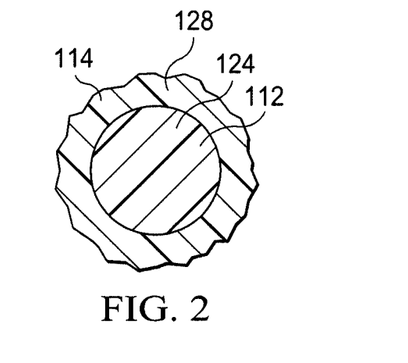
FIG. 2 is a schematic, cross-sectional view taken alone line 2-2 in FIG. 1B.

Referring to the drawings and primarily to FIGS. 1A-2, an illustrative, non-limiting embodiment of a reduced-pressure treatment system 100 for treating a tissue site 102, e.g. a wound 104, is presented. The wound 104 may include, without limitation, any irregularity with a tissue, such as an open wound, surgical incision, or diseased tissue. The wound 104 may involve various tissues: epidermis 106 (or generally skin), dermis 108, and subcutaneous tissue 110. The reduced-pressure treatment system 100 may be used to treat the tissue site 102, such as a wound 104 of any depth, as well as many different types of wounds including open wounds. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

In the illustrative, non-limiting embodiment, the reduced-pressure treatment system 100 generally includes a manifold pad 111, a sealing drape 116, and a reduced-pressure subsystem 118. The manifold pad 111 includes a manifold member 112 and a hydrogel reservoir member 114. The manifold pad 111 has a tissue-facing side 122 and is operable at a first pressure ($P_1$) to receive and hold, or store, fluids and, in particular, the hydrogel reservoir member 114 stores the fluids. When the reduced pressure, or negative pressure, is increased, i.e., absolute pressure is decreased, to a second pressure ($P_2$), the manifold pad 111 may distribute the reduced pressure, allow fluids to flow through the manifold pad 111, and release at least a portion of the previously stored fluids from the hydrogel reservoir member 114. The manifold pad 111 will be further described below.

The sealing drape 116 provides a fluid seal over the tissue site 102. The reduced-pressure treatment system 100 may include an attachment device 120. The sealing drape 116 and attachment device 120 form a fluid seal between the sealing drape 116 and the patient's epidermis 106. The manifold pad 111 is positioned between a tissue-facing (inward-facing) side 132 of the sealing drape 116 and the tissue site 102. "Fluid seal," or "seal," means a seal adequate to maintain reduced pressure at a desired site given the particular reduced-pressure source or subsystem involved.

The term "manifold" as used herein generally refers to a substance or structure that is provided to assist in applying reduced pressure to, delivering fluids to, or removing fluids from a tissue site, e.g., the tissue site 102. The manifold member 112 typically includes a plurality of flow channels or pathways to distribute fluids provided to and remove fluids from around the manifold member 112. The plurality of flow channels or pathways may be interconnected. The manifold member 112 may be a biocompatible material that is capable of being placed in contact with a tissue site, e.g., the tissue site 102, and distributing reduced pressure to the tissue site 102. Examples of manifold members may include, without limitation, devices that have structural elements arranged to form flow channels, such as, for example, cellular foam, open-cell foam, porous tissue collections, liquids, gels, and foams that include, or cure to include, flow channels. The manifold member 112 may be porous and may be made from foam, gauze, felted mat, etc. The manifold member 112 may be formed from a porous material, e.g., a foam, or from a material that is made porous, e.g., a solid member in which apertures have been applied.

In one illustrative, non-limiting embodiment, the manifold member 112 is a porous foam that includes a plurality of interconnected struts 124. The interconnected struts 124 may help form a plurality of interconnected cells or pores 126, which act as flow channels through the manifold member 112. The porous foam may be a polyurethane, open-cell, reticulated foam, such as a GranuFoam® material manufactured by Kinetic Concepts, Incorporated of San Antonio, Tex. In one illustrative, non-limiting embodiment, the pores 126 may have a pore size (pores per inch (ppi)) between 20 ppi and 60 ppi.

The hydrogel reservoir member 114 is associated with the manifold member 112 and is operable at a first pressure ($P_1$) to receive and hold, or store, a fluid, such as exudate or any other fluid, from the tissue site 102 and is operable at a second pressure ($P_2$) to release at least a portion of the absorbed fluid. The first pressure is greater than the second pressure on an absolute pressure scale, i.e., $P_1 > P_2$. In one illustrative embodiment, the first pressure is substantially atmospheric pressure (gauge pressure 0 mm Hg and an absolute pressure at sea level of about 760 mm Hg). In an alternative embodiment, the first pressure is a hydrostatic pressure at the tissue site 102. As will be discussed further below, the second pressure is generally a reduced pressure as provided by the reduced-pressure subsystem 118 for treatment of the tissue site 102 and is generally in the range of −75 mm Hg to −500 mm Hg (gauge pressure).

The manifold pad 111, which has the hydrogel reservoir member 114, distributes (or manifolds) reduced pressure under the influence of a reduced pressure, e.g., the second pressure ($P_2$). When the reduced pressure is decreased (the pressure is raised in terms of absolute pressure), e.g., to the first pressure ($P_1$), due to an equipment failure or other reason, the fluids continue to be removed from the tissue site 102 but are now stored in the hydrogel reservoir 114 of the manifold pad 111. When the reduced pressure is increased, e.g., to the second pressure ($P_2$), the fluid is removed, at least in part, from the hydrogel reservoir 114, and the manifold pad 111 distributes the reduced pressure to the tissue site 102. In one illustrative embodiment, the hydrogel reservoir member 114 releases between 20% and 80% of the absorbed, or stored, fluid when placed under the influence of the greater reduced pressure (lower absolute pressure), e.g., the second reduced pressure ($P_2$).

The hydrogel reservoir member 114 may be formed from any suitable hydrogel material. Hydrogels, include without limitation, any superaborbent natural or synthetic polymers, such as hydrophilic cross-linked polymers. Illustrative, non-limiting examples of suitable hydrogels include acrylics, e.g., acrylic acid, methacrylic acid and their salts; sulphonates, e.g., amps (acrylamido-2-methyl-propanosulfonic acid, and their salts), carboxy methyl cellulose (CMC), and alginates. In some embodiments, the hydrogel material is an ionic hydrogel. Additionally, the hydrogel reservoir member 114 may also incorporate biocides, antimicrobial agents, electrically conductive materials for pain management, visual indicators to, for example, indicate saturation, and other materials.

The hydrogel reservoir member 114 may be associated with the manifold member 112 in numerous ways. As a non-limiting, illustrative example, the manifold member 112 may be coated with the hydrogel material. In some embodiments, the hydrogel reservoir member 114 may be directly coupled to the manifold member 112 or the hydrogel reservoir member 114 may be placed adjacent to the manifold member 112. As used herein, the term "coupled" generally includes coupling via a separate object and includes direct coupling. The term "coupled" also encompasses two or more components that are continuous with one another by virtue of each of the components being formed from the same piece of material. Also, the term "coupled" may include chemical, mechanical, thermal, or electrical coupling. Fluidly coupling means that fluid is in communication between the designated parts or locations.

In the illustrative, non-limiting embodiment of FIGS. 1A-2, the hydrogel reservoir member 114 is a hydrogel coating 128 that is applied to at least one of the interconnected struts 124 of the manifold member 112. The hydrogel coating 128 may be applied by any suitable technique. In one illustrative embodiment, the hydrogel coating 128 is applied to the manifold member 112 by first immersing at least a portion of the manifold member 112, or substrate, into a liquefied, or partially liquefied, hydrogel. The hydrogel may be supplied as a non-crosslinked solution, dispersion, solid (hot melt or powder), or emulsion. The non-crosslinked solution is then either activated during the impregnation process (e.g., using UV light) or immediately before the impregnation process, such that the crosslinking process continues within the manifold member 112, or substrate. In another illustrative, non-limiting embodiment, the crosslinking may be achieved during a separate process, such as coincident with a sterilization process using gamma or e-beam irradiation. As another illustrative, non-limiting embodiment, a pre-crosslinked gel, is supplied as a suspension or emulsion and may be used to impregnate the manifold member 112.

Regardless of the approach used, at least a portion of the interconnected struts 124 are coated with the hydrogel. All or substantially all of the interconnected struts 124 may be coated with a hydrogel. Excess hydrogel from immersion may then be removed from the manifold member 112 by squeezing the manifold member 112 such that the excess hydrogel is released from the manifold member 112. The remaining hydrogel on the manifold pad 111 adheres to the interconnected struts 124, dries, and forms a hydrogel coating 128 about the interconnected struts 124. Alternatively, the hydrogel may be sprayed over at least a portion of the manifold member 112 whereby at least a portion of the interconnected struts 124 receive the hydrogel coating 128. Alternatively, the hydrogel may be applied using a blade coating or offset-roll coating. The manifold pad 111 is covered with the sealing drape 116.

The sealing drape 116 includes a first side 130 and a tissue-facing (inward-facing) side 132. The sealing drape 116 may be sized so that the sealing drape 116 overlaps the wound 104 in such a manner that a portion of the sealing drape 116 form a drape extension 134. the drape extension 134 extends beyond the periphery of the wound 104. The sealing drape 116 may be any material that provides a fluid seal. The sealing drape 116 may, for example, be an impermeable or semi-permeable, elastomeric material. "Elastomeric" means having the properties of an elastomer. It generally refers to a polymeric material that has rubber-like properties. More specifically, most elastomers have an ultimate elongation greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional examples of sealing drapes 116 include a silicone drape, 3M Tegaderm® drape, PU drape such as one available from Avery Dennison Corporation of Pasadena, Calif.

The attachment device 120 may be used to hold the sealing drape 116 against the patient's epidermis 106 or another layer, such as a gasket or additional sealing member. The attachment device 120 may take numerous forms. For example, the attachment device 120 may be a medically acceptable, pressure-sensitive adhesive that is applied to the drape extensions 134 of the sealing drape 116. Alternatively, the pressure-sensitive adhesive may span the entire width of the sealing drape 116. Alternative attachment devices 120 may include, but are not limited to, heat-activated adhesives, sealing tapes, double-sided sealing tapes, pastes, hydrocolloids, hydrogels, hooks, or sutures.

The reduced-pressure subsystem 118 includes a reduced-pressure source 136. The reduced-pressure source 136 provides reduced pressure, e.g., the second reduced pressure ($P_2$), as a part of the reduced-pressure treatment system 100. As used herein, "reduced pressure" generally refers to a pressure less than the ambient pressure at the tissue site 102 that is being subjected to treatment. In most cases, this reduced pressure will be less than the atmospheric pressure at which the patient is located. Alternatively, the reduced pressure may be less than a hydrostatic pressure at the tissue site 102. Reduced pressure may initially generate fluid flow in the manifold pad 111, a reduced-pressure delivery conduit 138, or conduit 138, and proximate the tissue site 102, e.g., the wound 104. As the hydrostatic pressure around the tissue site 102, e.g. the wound 104, approaches the desired reduced pressure, the flow may subside, and the reduced pressure may be maintained. The reduced pressure delivered may be constant, varied (patterned or random) and may be delivered continuously or intermittently. Although the terms "vacuum" and "negative pressure" may be used to describe the pressure applied to the tissue site 102, the actual pressure applied to the tissue site 102 may be more than the pressure normally associated with a complete vacuum. Consistent with the use herein, an increase in reduced pressure or vacuum pressure typically refers to a relative reduction in absolute pressure.

The reduced-pressure source 136 may be involve any technique or be any device for supplying a reduced pressure, such as a vacuum pump or wall suction. While the amount and nature of reduced pressure applied to the tissue site 102 will typically vary according to the application, the reduced pressure will typically be between −5 mm Hg and −500 mm Hg (gauge pressure).

In the illustrative, non-limiting embodiment of FIG. 1, the reduced-pressure source 136 has a battery compartment 140 and a canister 142 with windows 144 providing a visual indication of the level of fluid within canister 142. An interposed membrane filter, such as hydrophobic or oleophobic filter, may be interspersed between the reduced-pressure delivery conduit 138 and the reduced-pressure source 136.

The reduced pressure developed by the reduced-pressure source 136 is delivered through the reduced-pressure delivery conduit 138 to a reduced-pressure interface 146, which may be an elbow port 148. In one illustrative, non-limiting embodiment, the elbow port 148 is a TRAC® technology port available from Kinetic Concepts, Inc. of San Antonio, Tex. The reduced-pressure interface 146 allows the reduced pressure to be delivered to the sealing drape 116 and realized within an interior portion below the sealing drape 116 and further realized within the manifold member 112. In this illustrative, non-limiting embodiment, the elbow port 148 extends through the sealing drape 116 and to the manifold member 112, but numerous arrangements are possible.

According to an illustrative, non-limiting embodiment, in operation, the manifold pad 111 may be placed proximate the tissue site 102, e.g., the wound 104. The sealing drape 116 may be placed over the manifold pad 111 such that the drape extension 134 extends beyond a periphery of the wound 104. The drape extension 134 may be secured to the patient's epidermis 106 by the attachment device 120 in order to form a fluid seal over the tissue site 102 and the manifold pad 111. The reduced-pressure interface 146 may then be applied, if not already installed. The reduced-pressure delivery conduit 138 is fluidly coupled to the reduced-pressure interface 146 and fluidly coupled to the reduced-pressure source 136.

The reduced-pressure subsystem 118 may be activated so that reduced pressure is delivered into the reduced-pressure delivery conduit 138. Under a reduced pressure ($P_2$), fluids will be delivered from the tissue site 102 to the manifold pad 111 and through reduced-pressure delivery conduit 138 to canister 142. During this operation if an event occurs such that the reduced pressure is decreased, e.g., the pressure goes from $P_2$ to $P_1$, fluid flow in the reduced-pressure delivery conduit 138 may cease, and yet fluids may continue to be removed from the tissue site 102 and stored away from the tissue site 102 by the hydrogel reservoir member 114 of the manifold pad 111. When the reduced pressure is restored, e.g., the pressure goes from $P_1$ to $P_2$, the fluid will again flow in the reduced-pressure delivery conduit 138 and be delivered to the canister 142 and all or a portion of the fluid in the hydrogel reservoir member 114 will be released.

According to another illustrative, non-limiting embodiment, in operation, after the manifold member 112 is placed adjacent to the tissue site 102, fluid associated with the tissue site 102, e.g., the exudates or other fluids associated with the tissue site 102, may begin to be absorbed by the hydrogel coating 128 even though reduced pressure ($P_2$) has not been applied. The hydrogel coating 128 is, however, adapted to receive at least a portion of the fluid from the tissue site 102 at the existing pressure ($P_1$). In other words, the hydrogel coating 128 may be adapted to draw fluid from the tissue site 102 without the delivery of reduced pressure thereto, and this fluid removal may be beneficial for treatment and healing at the tissue site 102 when reduced pressure is not available. As the hydrogel coating 128 absorbs the fluid, the hydrogel coating 128 swells into adjacent pore(s) 126 thereby closing the pores 126 such that additional fluid at the tissue site 102 is diverted to other areas of the manifold member 112 not yet exposed to fluid and the fluid is absorbed by the hydrogel coating 128. Reduced pressure may then be used to remove fluids.

Once the reduced-pressure source 136 is activated, a reduced pressure is delivered to the interior of the sealing drape 116 and the manifold pad 111. As the reduced pressure ($P_2$) is delivered, the hydrogel coating 128 releases at least a portion of the previously absorbed, or stored, fluid. As the absorbed fluid is released by the hydrogel coating 128, the hydrogel coating 128 shrinks and the interconnected pores 126 open. Additional fluid from the tissue site 102 may then be drawn into the manifold pad 111 via the interconnected pores 126. Thus, the reduced-pressure treatment system 100 may be operable to remove at least some fluid from the tissue site 102 with or without delivery of a reduced pressure. With the continued delivery of reduced pressure, fluid from the tissue site 102 passes through the manifold pad 111 via the interconnected pores 126, into the reduced-pressure interface 146, through the reduced-pressure delivery conduit 138, and into the canister 142 of the reduced-pressure source 136.

Referring now primarily to FIGS. 3A-3E, another illustrative, non-limiting embodiment of a manifold pad 211 for use with a reduced-pressure treatment system, e.g., the reduced-pressure treatment system 100 of FIG. 1A, is presented. The manifold pad 211 includes a hydrogel reservoir member 214 that is associated with a manifold member 212. In the illustrative, non-limiting embodiment of FIGS. 3A-3C, the hydrogel reservoir member 214 comprises one or a plurality of hydrogel beads 250, which may be in spaced relationship relative to one another. The hydrogel beads 250 may be formed from an ionic hydrogel or any of the materials previously mentioned for the hydrogel reservoir member 114. Some of the hydrogel beads 250 may include an antimicrobial agent, such as ionic silver or any other suitable antimicrobial agent. Alternatively or in addition, antimicrobial beads (not shown), formed from any suitable antimicrobial agent, such as ionic silver, may be disposed in the manifold member 212 adjacent to the hydrogel beads 250.

The hydrogel beads 250 may be disposed within the manifold member 212 via any suitable technique. For example, the hydrogel beads 250 may be injected into the manifold member 212 by using a syringe or a syringe-like implement. Alternatively, the manifold member 212 may be formed around the hydrogel beads 250. In one illustrative, non-limiting embodiment shown in FIG. 3B, the manifold member 212 has a height ($h_1$) and the hydrogel beads 250 are disposed within the upper third ($h_2$) of the manifold member 212 for the orientation shown. However, it will be appreciated that the hydrogel beads 250 may be disposed at any suitable position within the manifold member 212 relative to the manifold member 212.

Figure 3A:
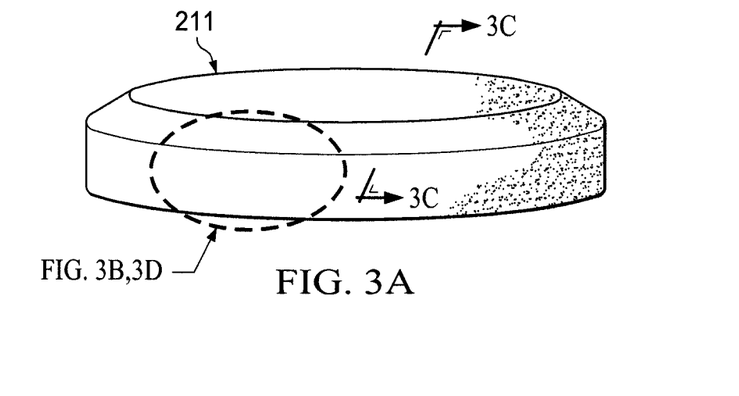
FIG. 3A is a schematic, perspective view of an illustrative, non-limiting embodiment of a manifold pad for use as part of an illustrative, non-limiting embodiment of a reduced-pressure wound treatment system.
Figure 3B:
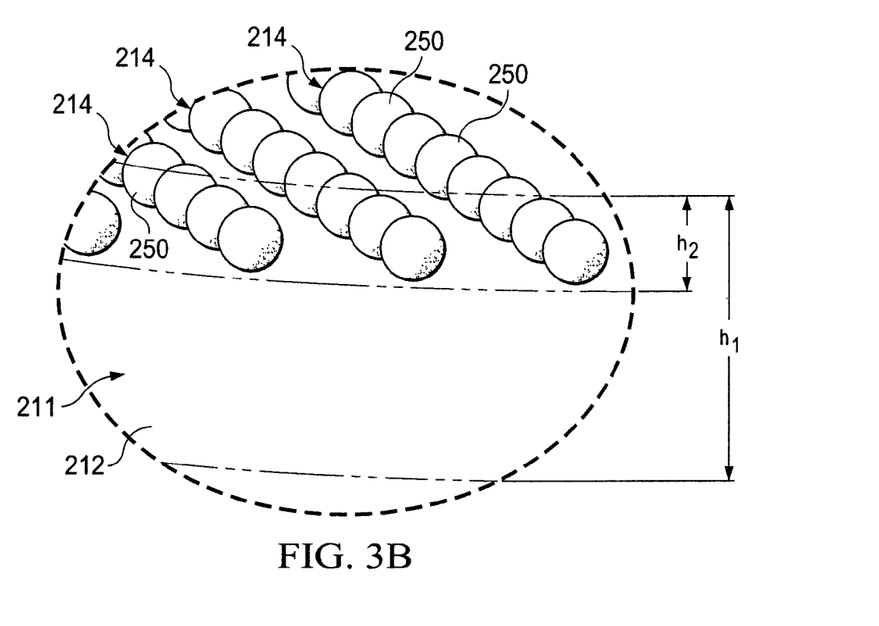
FIG. 3B is an enlarged, schematic, perspective view of a portion of an illustrative, non-limiting embodiment of a manifold pad employing hydrogel beads.
Figure 3C:
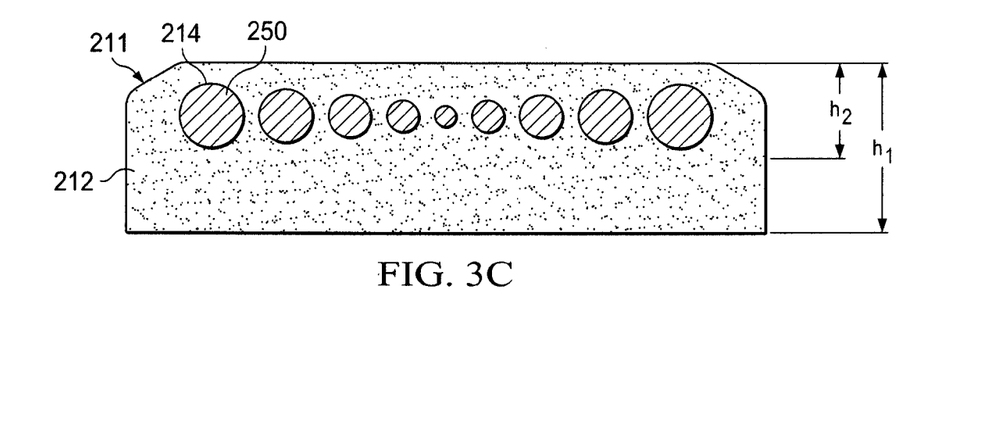
FIG. 3C is an enlarged, schematic, cross-sectional view of a portion of an illustrative manifold pad employing hydrogel beads.
Figure 3D:
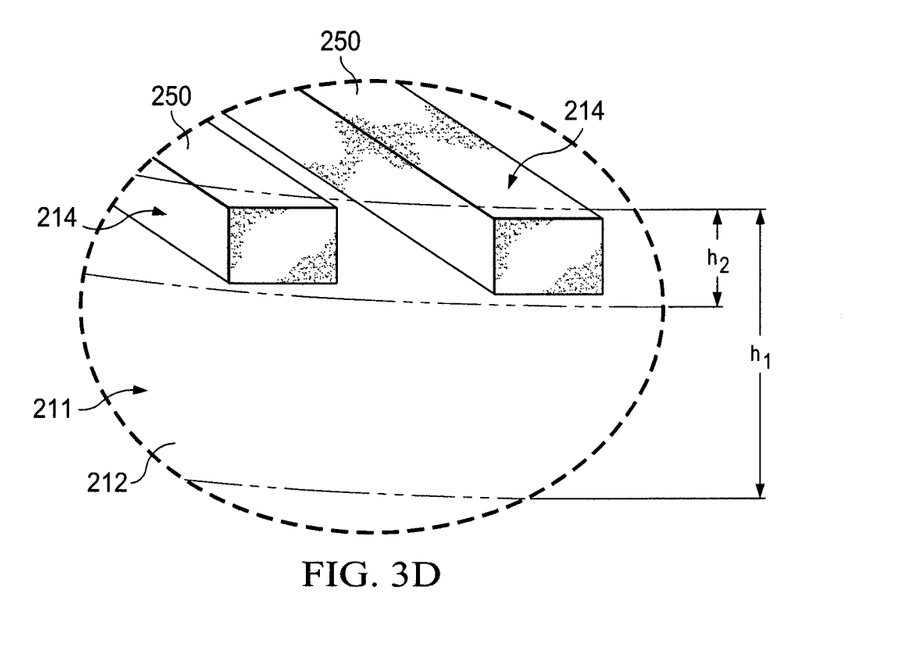
FIG. 3D is an enlarged, schematic, perspective view of a portion of an alternative manifold pad employing hydrogel beads.
Figure 3E:
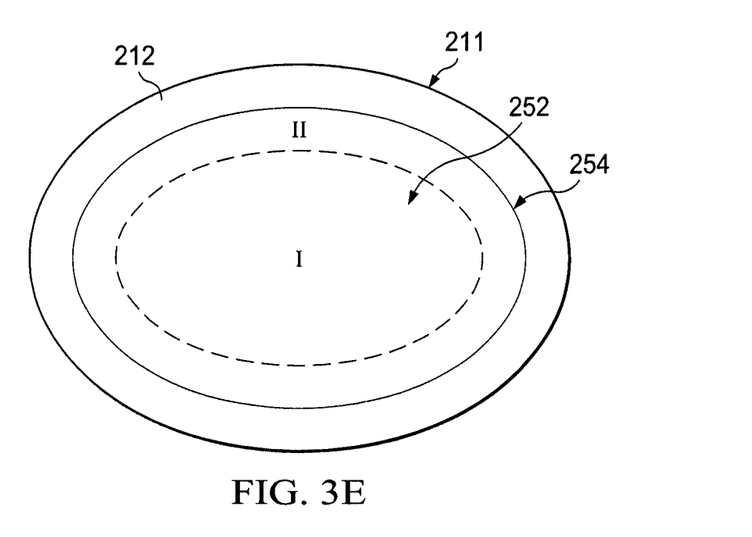
FIG. 3E is a schematic, top view of the manifold pad of FIG. 3A.

Referring now primarily to FIG. 3E, in some embodiments, the manifold member 212 may include a first zone 252, which is nearest the center of the manifold member 212, and a second zone 254, or peripheral portion, which is nearest the periphery of the manifold member 212. In some embodiments, the second zone 254 of the manifold member 212 includes a greater amount of hydrogel relative to the first zone 252 of the manifold member 212. For example, the hydrogel beads 250 located in the second zone 254 may have a greater diameter or density than the hydrogel beads 250 located in the first zone 252.

In another illustrative, non-limiting embodiment shown in FIG. 3C, the diameter of a given hydrogel beads 250 may be proportional to the distance the hydrogel bead 250 is from the center of the manifold member 212. For example, the hydrogel beads 250 nearest the periphery of the manifold member 212 are the largest and the hydrogel beads 250 become gradually smaller as the hydrogel beads 250 get closer to the center of the manifold member 212. In yet another illustrative, non-limiting embodiment, the density of hydrogel beads 250 may be varied. That is the number of hydrogel beads 250 located in the second zone 254 may be greater than the number of hydrogel beads 250 located in the first zone 252. Also, the hydrogel beads 250 may take any suitable shape. For example, as shown in FIGS. 3B and 3C, the hydrogel beads 250 may be spherically shaped (spheroids). Alternatively, as shown in FIG. 3D, the hydrogel beads 250 may have an elongated square bar shape. The hydrogel beads 250 may also be teardrop-shaped, polygon, irregular shaped, or another shape. It will be appreciated that the hydrogel beads 250 may have any suitable shape or size.

According to an illustrative, non-limiting embodiment, in operation, the manifold member 212 is placed proximate a tissue site (e.g., the tissue site 102 in FIG. 1A) and a sealing drape may be used to form a fluid seal. Under reduced pressure ($P_2$), the manifold member 212 distributes reduced pressure with only minimal absorption of fluid. When the reduced pressure is decreased (absolute pressure increased) to ($P_1$), fluid from the tissue site enters the manifold member 212 but is absorbed by the hydrogel beads 250. In embodiments where the greatest amount of hydrogel is located nearest the periphery of the manifold member 212, the hydrogel beads 250 nearest the center of the manifold member 112 will generally become saturated with fluid from the tissue site first, and thereafter additional fluid from the tissue site is diverted towards the hydrogel beads 250 nearest the periphery of the manifold member 212 for absorption.

When a reduced pressure is delivered or restored to the manifold member 212, as discussed in relation to FIGS. 1-2, the hydrogel beads 250 release at least a portion of the previously absorbed, or stored, fluid. As the fluid from the hydrogel beads 250 is released, the hydrogel beads 250 shrink and fluid from the tissue site is permitted to pass through the manifold member 212 and ultimately to a canister of a reduced-pressure subsystem. Thus, the reduced-pressure treatment system may be operable to remove at least some fluid from the tissue site with or without delivery of a reduced pressure thereto.

Figure 4A:
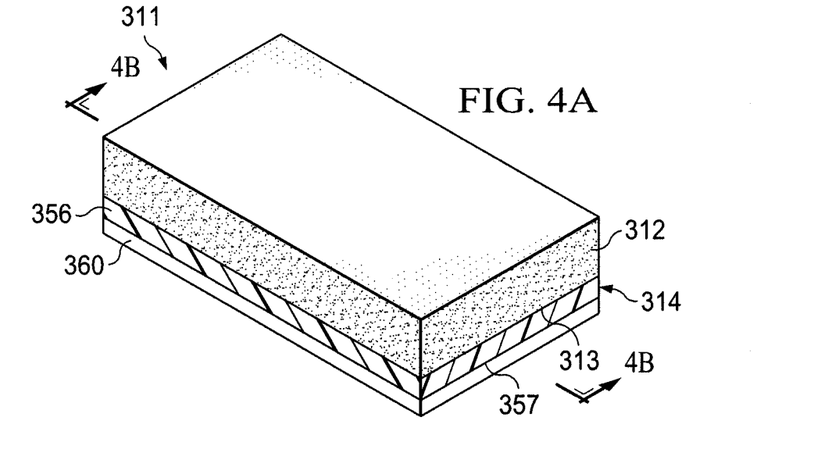
FIG. 4A is a schematic, perspective view of an illustrative, non-limiting embodiment of a manifold pad for use as part of an illustrative, non-limiting embodiment of a reduced-pressure wound treatment system.
Figure 4B:
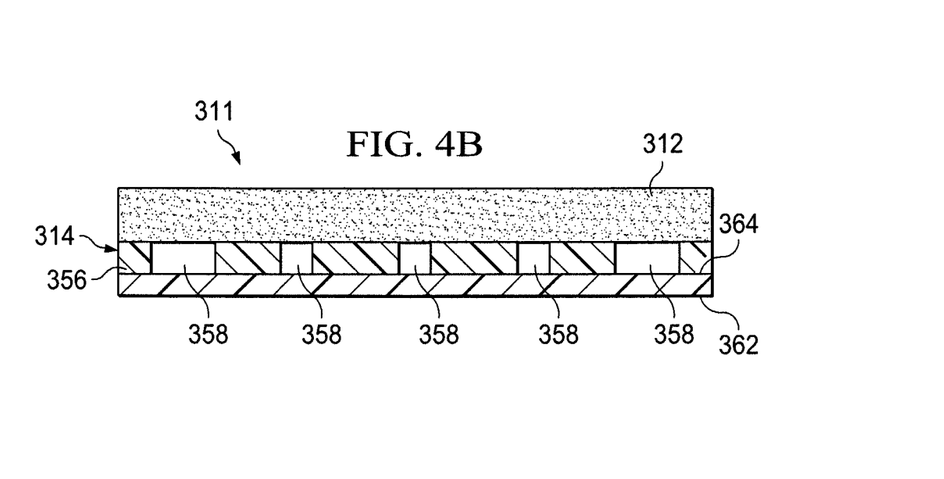
FIG. 4B is a schematic, cross-sectional view of the manifold pad of FIG. 4A taken along line 4B-4B.
Figure 4C:
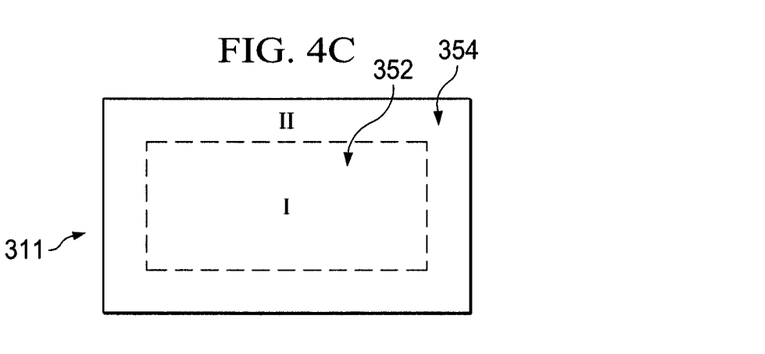
FIG. 4C is a schematic, top view of the manifold pad of FIG. 4A.

Referring now primarily to FIGS. 4A-4C, another illustrative, non-limiting embodiment of a manifold pad 311 that may be used with a reduced-pressure treatment system, such as the reduced-pressure treatment system 100 of FIG. 1A, is presented. The manifold pad 311 includes a hydrogel reservoir member 314 associated with a manifold member 312. The hydrogel reservoir member 314 is a hydrogel sheet 356 disposed adjacent to the manifold member 312 proximate a tissue-facing side 313 of the manifold member 312. The hydrogel sheet 356 may abut the manifold member 312, be laminated with the manifold member 312, or be coupled to the manifold member 312. Alternatively, the hydrogel sheet 356 may be cast with, co-extruded with, or otherwise formed with the manifold member 312. The hydrogel sheet 356 may be formed from any suitable hydrogel material, such as those previously mentioned. In some embodiments, the hydrogel sheet 356 is formed from an ionic hydrogel material.

The hydrogel sheet 356 may include one or more apertures 358. The hydrogel sheet 356 may include a first zone 352 that is nearest the center of the hydrogel sheet 356 and a second zone 354 that is nearest the periphery of the hydrogel sheet 356. The size or number of the apertures 358 located in the second zone 354 of the hydrogel sheet 356 may be greater than the size or number of apertures 358 located in the first zone 352. Alternatively, and as best shown in FIG. 4B, the size of the apertures 358 may be proportional to the distance a given aperture is from the center of the hydrogel sheet 356. For example, the apertures 358 nearest the periphery of the hydrogel sheet 356 are the largest and the apertures 358 become gradually smaller the closer the apertures 358 are to the center of the hydrogel sheet 356. The apertures 358 may have any suitable shape, including, but not limited to, circular, elliptical, triangular, square, rectangular, hexagonal, octagonal, irregular, or other shape. In some embodiments, the diameter of the apertures 358 may be within the range of about 1 mm to about 10 mm. In some embodiments, the distance (d) between adjacent apertures 358 may be in the range of abut 1 mm to about 10 mm.

In some embodiments, including the manifold pad 311 that is presented in FIGS. 4A-4C, a wicking layer 360 may be disposed adjacent to a tissue-facing side 357 of the hydrogel sheet 356 such that the hydrogel sheet 356 is disposed between the wicking layer 360 and the manifold member 312. The wicking layer 360 may abut the hydrogel sheet 356, be laminated with the hydrogel sheet 356, or otherwise coupled to the hydrogel sheet 356. The wicking layer 360 may be operable to transmit fluid from a tissue-facing side 362 of the wicking layer 360 to a first side 364. The wicking layer 360 may also be operable to, or adapted to, manifold an applied reduced pressure.

The wicking layer 360 may be formed from any suitable material, including, but not limited to a non-woven material, such as a non-woven rayon sheet, non-woven polyester, polyamide, polyolefine, compressed fiber blocks (e.g., formed from polyester, or polyamide, or polyolefine fibers), or a sintered polymer (e.g., polyolefine, EVA, polyamide, or other polymer.), a reticulated foam, or another non-woven material. In some embodiments, the wicking layer 360 may be treated, or otherwise modified, to be hydrophilic. In some embodiments, the wicking layer 360 and hydrogel sheet 356 may be employed without the use of the manifold member 312.

According to an illustrative, non-limiting embodiment, in operation, the tissue-facing side 362 of the wicking layer 360 is placed proximate the tissue site. The wicking layer 360 receives fluid from the tissue site and transports the fluid from the tissue-facing side 362 to the first side 364. Once the fluid has passed the wicking layer 360, the fluid may be transmitted under the influence of reduced pressure ($P_2$) through the manifold member 312 and eventually to a canister or other location. During operation with reduced pressure applied, the hydrogel reservoir member 314 may absorb some of the fluid. When the reduced pressure is removed or is decreased (absolute pressure increased), e.g., to $P_1$, the hydrogel sheet 356 stores additional fluid. As the hydrogel sheet 356 absorbs the fluid, the hydrogel sheet 356 swells and the apertures 358 begin to shrink.

When a reduced pressure is delivered or restored, e.g., to $P_2$, the hydrogel sheet 356 releases at least a portion of the previously absorbed, or stored, fluid. Once the hydrogel sheet 356 begins to release the fluid, the apertures 358 begin to increase in diameter thereby allowing fluid to pass from the tissue site, through the wicking layer 360, through the apertures 358 that are through the hydrogel sheet 356, into the manifold member 312 and ultimately to a canister of a reduced-pressure source. Thus, the reduced-pressure treatment system may be operable to remove at least a portion of fluid from the tissue site with and without the delivery of a reduced pressure thereto.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A reduced-pressure treatment system for treating a tissue site on a patient, the reduced-pressure treatment system comprising:
   a manifold pad for disposing proximate the tissue site, the manifold pad comprising:
      a manifold member, and
      a hydrogel reservoir member impregnated within the manifold member, the hydrogel reservoir member adapted to receive and store a fluid from the tissue site at a first pressure and adapted to release at least a portion of the fluid at a second pressure, wherein the first pressure is greater than the second pressure on an absolute pressure scale;
   a sealing drape for placing over the tissue site and the manifold pad, the sealing drape adapted to form a fluid seal; and
   a reduced-pressure subsystem for delivering reduced pressure to the manifold pad.

2. The reduced-pressure treatment system of claim 1, wherein the first pressure is substantially atmospheric pressure.

3. The reduced-pressure treatment system of claim 1, wherein the first pressure is a hydrostatic pressure proximate to the tissue site.

4. The reduced-pressure treatment system of claim 1, wherein the hydrogel reservoir member is adapted to release between 20% and 80% of the stored fluid under the influence of the second pressure.

5. The reduced-pressure treatment system of claim 1, wherein the manifold member comprises a porous foam having interconnected struts within an interior portion of the manifold member, and the hydrogel reservoir member is a hydrogel coating applied to the interconnected struts within the interior portion of the manifold member.

6. The reduced-pressure treatment system of claim 1, wherein the hydrogel reservoir member comprises a plurality of hydrogel beads disposed within the manifold member, and each of the plurality of hydrogel beads has a diameter proportional to a distance from a center of the manifold member.

7. The reduced-pressure treatment system of claim 1, wherein the manifold member comprises a porous foam having interconnected struts within an interior portion of the manifold member, and the hydrogel reservoir member comprises an ionic hydrogel coating applied to the interconnected struts within the interior portion of the manifold member.

8. A manifold pad for treating a tissue site of a patient, the manifold pad comprising:
    a manifold member adapted to distribute reduced pressure;
    a hydrogel reservoir member impregnated within the manifold member; and
    wherein the hydrogel reservoir member is adapted to receive and store a fluid from the tissue site at a first pressure and adapted to release at least a portion of the fluid at a second pressure, wherein the first pressure is greater than the second pressure on an absolute pressure scale.

9. The manifold pad of claim 8, wherein the manifold member comprises a foam having a plurality of interconnected struts within an interior portion of the manifold member; wherein the hydrogel reservoir member comprises a hydrogel coating; and wherein at least a portion of the plurality of interconnected struts within the manifold member are at least partially coated with the hydrogel coating.

10. The manifold pad of claim 8, wherein the hydrogel reservoir member is an ionic hydrogel.

11. The manifold pad of claim 8, wherein the hydrogel reservoir member is adapted to release between 20% and 80% of the absorbed fluid under the influence of reduced pressure.

12. The manifold pad of claim 8, wherein:
    wherein the hydrogel reservoir member comprises a plurality of hydrogel beads disposed within an interior portion of the manifold member; and
    wherein each of the plurality of hydrogel beads has a diameter proportional to a distance from a center of the manifold member.

13. The manifold pad of claim 8, wherein:
    the manifold member includes a central portion and a peripheral portion;
    a first plurality of hydrogel beads is disposed within the central portion; and
    a second plurality of hydrogel beads is disposed within the peripheral portion and the second plurality of hydrogel beads is more numerous than the first plurality of hydrogel beads.

14. The manifold pad of claim 8, wherein:
    the manifold member includes a central portion and a peripheral portion;
    a plurality of hydrogel beads are disposed within the central portion and within the peripheral portion; and
    a first diameter of each of the hydrogel beads disposed within the peripheral portion is greater than a second diameter of the hydrogel beads disposed within the central portion.

15. The manifold pad of claim 13, wherein a cross-section of each of the first plurality of hydrogel beads and the second plurality of hydrogel beads is circular.

16. The manifold pad of claim 12, wherein the manifold member has a height ($h_1$), a tissue-facing side, and a first side; and wherein the plurality of hydrogel beads is disposed within one third (⅓) $h_1$ from the first side of the manifold member.

17. A manifold pad for treating a tissue site on a patient, the manifold pad comprising:
    a manifold member comprising a first material of interconnected struts within the manifold member forming a plurality of interconnected cells through the manifold member; and
    a reservoir member comprising a second material coating at least a portion of the interconnected struts within the manifold member;
    wherein the first material and the second material are different materials;
    wherein the second material is a super absorbent polymer that is adapted to receive and retain liquids from the tissue site at a first pressure and is adapted to release a substantial portion of the liquids at a second pressure.

\* \* \* \* \*